(12) United States Patent
Effing et al.

(10) Patent No.: US 6,193,996 B1
(45) Date of Patent: Feb. 27, 2001

(54) DEVICE FOR THE TRANSDERMAL DELIVERY OF DICLOFENAC

(75) Inventors: Jochem J. Effing, Bachhagel; Anja N. Becker, Bottrop; Carsten Coors, Borken, all of (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/276,630

(22) Filed: Mar. 25, 1999

Related U.S. Application Data

(60) Provisional application No. 60/080,431, filed on Apr. 2, 1998.

(51) Int. Cl.$^7$ .................................................. A61K 9/70
(52) U.S. Cl. ........................ 424/449; 424/448; 514/567; 604/304
(58) Field of Search .................. 424/449, 448; 514/567, 825; 604/304, 890.1

(56) References Cited

U.S. PATENT DOCUMENTS

| | | | |
|---|---|---|---|
| 4,693,776 | * | 9/1987 | Krampe et al. .............................. 5/22 |
| 4,801,458 | * | 1/1989 | Hidaka et al. ........................ 424/443 |
| 5,176,916 | * | 1/1993 | Yamanaka et al. ................... 424/448 |
| 5,374,661 | * | 12/1994 | Betlach, II ......................... 514/772.4 |
| 5,505,956 | | 4/1996 | Kim et al. . |
| 5,744,162 | * | 4/1998 | Okabe et al. ......................... 424/486 |
| 5,993,849 | * | 11/1999 | Assmus et al. ....................... 424/449 |

FOREIGN PATENT DOCUMENTS

| | | |
|---|---|---|
| 0452837B1 | 10/1991 | (EP) . |
| 0524582B1 | 1/1993 | (EP) . |
| 0582727B1 | 2/1994 | (EP) . |
| 0 848 950 A2 | 6/1998 | (EP) . |
| 848950 A2 * | 6/1998 | (EP) . |
| 59-227819 | 12/1984 | (JP) . |
| 02202813 | 9/1993 | (JP) . |
| 7-233050 | 9/1995 | (JP) . |
| 07233050 | 11/1995 | (JP) . |
| 09143066 | 6/1997 | (JP) . |
| 9-143066 | 6/1997 | (JP) . |
| 91/09592 | 7/1991 | (WO) . |

* cited by examiner

*Primary Examiner*—Robert H. Harrison
(74) *Attorney, Agent, or Firm*—MarySusan Howard; Ted K. Ringsred; Robert W. Sprague

(57) ABSTRACT

The present invention provides a pressure sensitive skin adhesive comprising:
(a) a copolymer of one or more alkyl(meth)acrylates containing 4 to 12 carbon atoms in the alkyl group and one or more hydrophilic monomers;
(b) a mixture of penetration enhancers comprising:
  (i) an alkyl ester of an aliphatic monocarboxylic acid containing 1 to 5 carbon atoms in the alkyl group
  (ii) an alkyl pyrrolidone and
  (iii) an alkane polyol
(c) a therapeutically effective amount of diclofenac or a pharmaceutically acceptable salt thereof.

Further provided is a transdermal drug delivery device containing the pressure sensitive skin adhesive.

14 Claims, No Drawings

DEVICE FOR THE TRANSDERMAL DELIVERY OF DICLOFENAC

This is a continuation of Application No. 60/080431 filed Apr. 2, 1998.

FIELD OF THE INVENTION

The present invention relates to a transdermal drug delivery device for the delivery of diclofenac or a pharmaceutically acceptable salt thereof. In particular, the present invention relates to a pressure sensitive skin adhesive containing diclofenac or a pharmaceutically acceptable salt thereof.

BACKGROUND OF THE INVENTION

Ortho-[(2,6-dichlorophenyl)amino]phenylacetic acid (hereinafter referred to as diclofenac) and its pharmaceutically acceptable salts are known compounds useful in the treatment of inflammation. Sodium [ortho[(2,6-dichlorophenyl)amino]phenyl]acetate, also variously known as 2-[2,6-dichlorophenyl)amino]benzeneacetic acid mono-sodium salt and diclofenac sodium, has been shown, for example, in pharmacological studies to possess potent anti-inflammatory and analgesic properties. See, for example, Riess et al., *Scand. J. Rheumatol. Suppl.*, Vol. 22, pp. 17–29 (1978). The use of diclofenac sodium in the form of an aqueous solution in the treatment of ocular inflammation has also been shown. See, for example, M. Agata et al., *Nihon Ganka Gakkai* [Acta Soc. Ophthalmol. Japan], Vol. 87, pp. 19–28 (1983), and M. Agata et al., *Nihon Ganka Gakkai* [Acta Soc. Ophthalmol. Japan], Vol. 88, No. 6, pp. 61–66 (1984).

The transdermal delivery of diclofenac or its pharmaceutically acceptable salts has been described in various publications. For example, EP 524582 discloses a diclofenac sodium plaster. The plaster comprises a paste formulation that contains diclofenac sodium, a water-soluble polymer such as polyacrylic acid and a mixture of propylene glycol and l-menthol as penetration enhancers.

EP 582727 discloses a transdermal therapeutic formulation that comprises a polymer having lipophilic monomer units and hydrophilic monomer units in a weight ratio of 98:2 to 0:100, a drug, an alcohol and a penetration enhancer. As suitable polymers there are mentioned acrylic adhesives such as copolymers of alkyl acrylates and acrylic acid. Among the list of alcohols there are mentioned polyols such as propylene glycol. EP 582727 further discloses that known penetration enhancers can be used such as isopropyl myristate. Diclofenac is among the list of drugs that can be used in the transdermal therapeutic formulation.

EP 452837 discloses a medical adhesive comprising a plaster layer containing the following ingredients:

(1) a medicinal ingredient;
(2) a hydrophobic polymer having a glass transition temperature of −65° C. to 35° C.;
(3) a percutaneous absorption promoting agent;
(4) water, and
(5) a hydrophilic polymer which is soluble or capable of swelling in water.

The hydrophobic polymer is present in larger amounts than the hydrophilic polymer and the layer forms a water-in-oil type emulsion. It is disclosed that diclofenac can be used as the medicinal ingredient.

WO 91/09592 discloses a transdermal system with a reservoir layer that comprises a complex of the drug and a cyclo compound. The release rate of the drug from the system is controlled by the dissociation of the complex. Diclofenac is disclosed as one of the drugs that can be used in such a system.

U.S. Pat. No. 5,505,956 discloses the delivery of a drug such as diclofenac from a transdermal device that has on a backing an adhesive layer that has a laminate structure of 2 to 5 layers and each layer has different water absorption capacity. The adhesive layer contains an adhesive resin such as a polyacrylate, a penetration enhancer, a water adsorptive material such as a polyol and a lenitive agent. Pyrrolidone derivatives and higher fatty acid esters are mentioned as penetration enhancers.

SUMMARY OF THE INVENTION

It is an object of the present invention to provide a pressure sensitive skin adhesive that can be used for the manufacture of a transdermal drug delivery device for the transdermal delivery of diclofenac or a pharmaceutically acceptable salt thereof. It is further an object of the present invention to improve the transdermal delivery of diclofenac.

These objects have been accomplished by providing a pressure sensitive skin adhesive comprising:

(a) a copolymer of one or more alkyl(meth)acrylates containing 4 to 12 carbon atoms in the alkyl group and one or more hydrophilic monomers;
(b) a mixture of penetration enhancers comprising:
   (i) an alkyl ester of an aliphatic monocarboxylic acid containing 1 to 5 carbon atoms in the alkyl group,
   (ii) a 2-pyrrolidone derivative and
   (iii) an alkane polyol; and
(c) a therapeutically effective amount of diclofenac or a pharmaceutically acceptable salt thereof.

It has in particular been observed that the delivery of diclofenac or a pharmaceutically acceptable salt thereof is substantially improved by using the combination of penetration enhancers as set forth above.

The present invention further provides a transdermal drug delivery device using the above pressure sensitive skin adhesive and the use of the pressure sensitive skin adhesive for the manufacture of a transdermal drug delivery device for the treatment of inflammation or relief of pain. In addition, the invention provides a method of inducing analgesia in a subject comprising contacting the skin of the subject with a transdermal drug delivery device as described above and allowing the device to remain in contact with the skin for a time sufficient to establish or maintain a therapeutically effective blood level of diclofenac or a pharmaceutically acceptable salt thereof in the subject.

DETAILED DESCRIPTION OF THE INVENTION

The pressure sensitive skin adhesive of the present invention contains a copolymer of an alkyl acrylate and/or an alkyl methacrylate and at least one hydrophilic monomer. The alkyl group of the acrylate or methacrylate preferably contains 4 to 12 carbon atoms.

Examples of alkyl acrylates and alkyl methacrylates include n-butyl, n-pentyl, n-hexyl, cyclohexyl, isoheptyl, n-nonyl, n-decyl, isohexyl, isobornyl, 2-ethyloctyl, isooctyl, n-octyl and 2-ethylhexyl acrylates and methacrylates. Isooctyl acrylate is particularly preferred.

The hydrophilic monomers are typically monomers that have a tendency to bind or absorb water and are preferably monomers of which a homopolymer is capable of swelling in water or that can be dissolved in water. Examples of hydrophilic monomers include carboxylic acid containing monomers such as acrylic and methacrylic acid; hydroxy containing monomers such as 2-hydroxyethyl acrylate; vinyl containing monomers such as N-vinyl-2-pyrrolidone, vinylimidazoles, and vinyl acetate; mono-(meth)acrylates of poly(oxyalkylene), mono (meth)acrylates of poly(alkyleneoxide) alkyl ether; amides such as acrylamides, methacrylamides, N-vinyl valerolactam, and N-vinyl caprolactam; tetra-alkylammonium containing monomers such as (meth)acryloxyethyl trimethylammonium chloride, (meth) acryloxyethyl triethylammonium chloride, and (meth) acrylamido-ethyl trimethyl ammonium chloride; and amino group containing monomers such as dimethylaminoethyl (meth)acrylate, diethylamino (meth)acrylate, morpholino-ethyl (meth)acrylate, piperidino-ethyl (meth)acrylate, piperidino-ethyl-(meth)acrylamide, dimethylamino-ethyl (meth)acrylamide and diethylamino-ethyl (meth) acrylamide. A mixture of two or more hydrophilic monomers may also be used. Particularly preferred as a hydrophilic monomer is acrylic or methacrylic acid.

The copolymer may further comprise units that are derived from monomers other than the alkyl (meth)acrylate and the hydrophilic monomer. Examples of such further monomers that can be copolymerised with the (meth) acrylate and hydrophilic monomer include short chain (1 to 4 carbon atom) alkyl acrylates and methacrylates such as ethyl (meth)acrylate and methyl (meth)acrylate, acrylonitrile and styrene.

According to a particular embodiment of the present invention, the copolymer comprises units derived from a macromer that is copolymerizable with the alkyl (meth) acrylate and hydrophilic monomer. The macromer preferably has a weight average molecular weight between 5000 and 500000 as measured by GPC relative to a polystyrene standard, more preferably between 2000 and 10000 and most preferably between 5000 and 30000. Examples of suitable macromers include those described in WO96/8229 and in Krampe et al., U.S. Pat. No. 4,693,776, the disclosure of which is incorporated herein by reference, and in particular include polymethyl methacrylate macromer, polymethyl acrylate macromer, polystyrene macromer and polystyrene-acrylonitrile macromer.

Polymethyl methacrylate macromers are commercially available under the trade designation "ELVACITE" by ICI Acrylics (e.g., ELVACITE 1010, a polymethyl methacrylate macromonomer having an inherent viscosity of 0.070–0.080, a $T_g$ of 105° C., a GPC weight average molecular weight of 7,000–10,000, a GPC number average molecular weight of 2,500–4,000, and a polydispersity of 2.5–3.0, and ELVACITE 1020, a polymethyl methacrylate macromonomer having an inherent viscosity of 0.085–0.10, a $T_g$ of 105° C., a GPC weight average molecular weight of 12,000–15,000, a GPC number average molecular weight of 4,600–6,000, and a polydispersity of 2.5–3.0). A copolymer comprising units derived from a macromer as described above is particularly useful in a pressure sensitive skin adhesive of a transdermal drug delivery having a non-occlusive backing.

The weight ratio of monomer units derived from the alkyl(meth)acrylates to the monomer units derived from the hydrophilic monomers in the copolymer is typically between 98:2 and 80:20 and preferably between 96:4 and 88:12.

The copolymer of the pressure sensitive skin adhesive of this invention can be prepared by conventional free radical polymerization of the alkyl(meth)acrylates and hydrophilic monomers and optional further monomers and/or macromers copolymerizable therewith. The polymerization can be a solution- or emulsion polymerization and can be a thermally or photochemically initiated polymerization. Useful free radical initiators are known in the art and include azo compounds, such as azo-bisisobutyronitrile and 4,4'-azobis(-4-cyanovaleric acid), hydroperoxides such as cumene, t-butyl and t-amyl hydroperoxide, dialkyl peroxides such as di-t-butyl and dicumylperoxide, peroxyesters such as t-butylperbenzoate and di-t-butylperoxy phtalate, diacylperoxides such as benzoyl peroxide and lauroyl peroxide. Preferably the copolymer obtained is soluble in ethyl acetate and has an inherent viscosity ine the range 0.2 dl/g to about 2 dl/g, more preferably 0.4 dl/g to about 1.5 dl/g.

Diclofenac or a pharmaceutically acceptable salt thereof such as the sodium salt is present in the pressure sensitive skin adhesive in a "therapeutically effective amount." The latter term means that the concentration of the drug is such that in the composition it results in a therapeutic level of drug delivered over the term that the dosage form is to be used; e.g., that a therapeutically effective blood level of the drug is achieved or maintained. Such delivery is dependent on a great number of variables including, for example, the time period for which the individual dosage unit is to be used, and the flux rate of the drug from the system. The amount of drug needed can be experimentally determined. Generally, diclofenac or a pharmaceutically acceptable salt thereof is present in a device of the invention in an amount by weight of about 1 to about 12 percent, preferably about 3 to 8 percent, by weight based on the total weight of the pressure sensitive skin adhesive. In a preferred embodiment the pressure sensitive skin adhesive is free of solid undissolved drug.

The pressure sensitive skin adhesive of this invention contains a mixture of at least 3 different types of penetration enhancers, i.e. at least one alkyl ester of an aliphatic monocarboxylic acid containing 1 to 5 carbon atoms in the alkyl group, at least one 2-pyrrolidone derivative and at least one alkane polyol.

Preferably the alkyl ester of an aliphatic monocarboxylic acid is a lower alkyl (containing 1 to 6 carbon atoms) ester of an aliphatic monocarboxylic acid having 6 to 20 carbon atoms. Examples include isopropyl myristate, isopropyl palmitate, ethyl caprylate, methyl stearate, ethyl laurate, ethyl oleate, methyl oleate and propyl oleate. Isopropyl myristate is particularly preferred.

Preferred 2-pyrrolidone derivatives for use in the penetration enhancer mixture of the compositions are alkyl pyrrolidones, and particularly preferred are N-alkyl 2-pyrrolidone and derivatives thereof. Most preferred are N-alkyl 2-pyrrolidones wherein the alkyl-group contains from 6 to 14 carbon atoms. Examples of suitable 2-pyrrolidone derivatives include the esters of 2-pyrrolidone-5-carboxylic acid disclosed in U.S. Pat. No. 4,863,952 the disclosure of which is incorporated herein by reference; N-octyl 2-pyrrolidone; N-decyl 2-pyrrolidone and N-cetyl 2-pyrrolidone.

The alkane polyols for use in the penetration enhancer mixture of the invention are preferably lower alkane polyols having 2 to 5 carbon atoms. Specific examples include lower alkane diols such as ethylene glycol, propylene glycol, 1,3-propanediol, 1,2-butanediol, 1,3-butanediol, 1,4-butanediol, 2,3-butanediol and 1,5-pentanediol. Alkanetriols such as glycerin(1,2,3-propanetriol) can also be used. Propylene glycol is preferred.

According to a preferred embodiment of the present invention, the mixture of penetration enhancers is comprised of between 30 and 70% by weight of the alkyl ester of an aliphatic monocarboxylic acid, between 3 and 25% by weight of the 2-pyrrolidone derivative and between 20 and 45% by weight of the alkane polyol. A highly preferred mixture of penetration enhancers comprises between 45 and 65% by weight of isopropyl myristate, between 3 and 20% by weight of N-octyl pyrrolidone and between 25 and 40% by weight of propylene glycol. The total amount of penetration enhancers in the pressure sensitive skin adhesive is typically between 10 and 40% by weight of the total weight of the pressure sensitive skin adhesive.

The pressure sensitive skin adhesive of the present invention may further comprise a plasticizer or tackifying agent to improve the adhesive characteristics of the adhesive composition. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood resins or rosins.

The transdermal drug delivery device of the invention can be obtained by applying an adhesive layer containing the above described pressure sensitive skin adhesive to a backing. A transdermal drug delivery device in accordance with the invention can for example be prepared by dissolving the copolymer, the penetration enhancers and diclofenac or its pharmaceutically acceptable salt in an organic solvent (e.g., ethyl acetate) to afford a coating formulation. The coating formulation can be coated using conventional methods onto a suitable release liner to provide a predetermined uniform thickness of the coating formulation. Suitable release liners include conventional release liners comprising a known sheet material such as a polyester web, polyethylene web, or a polystyrene web, or a polyethylene-coated paper coated with a suitable fluoropolymer or silicone based coating. A preferred release liner is SCOTCHPAK™ 1022 film (3M, St. Paul, Minn.).

The adhesive coated release liner is then dried and laminated onto a backing using known methods. The backing can be occlusive, non-occlusive or a breathable film as desired. The backing is flexible such that it conforms to the skin. It can be any of the commonly used materials for pressure sensitive adhesive tapes, such as polyethylene, particularly low density polyethylene, linear low density polyethylene, high density polyethylene, randomly-oriented nylon fibres, polypropylene, ethylene-vinylacetate copolymer, polyurethane, rayon and the like. Backings that are layered, such as polyethylene-aluminium-polyethylene composites are also suitable. The backing should be substantially non-reactive with the ingredients of the formulation. Particularly preferred backings are SCOTCHPAK™ 1109 and COTRAN™ 9726 which are both occlusive backings available from 3M and COTRAN™ 9725 which is a non-occlusive backing available from 3M.

The transdermal drug delivery devices can be made in the form of an article such as a tape, a patch, a sheet, a dressing or any other form known to those skilled in the art. Generally the device will be in the form of a patch of a size suitable to deliver a predetermined amount of diclofenac or its pharmaceutically acceptable salt through the skin. Generally the device will have a surface area of about 10 cm$^2$ to about 100 cm$^2$ and preferably between 30 and 85 cm$^2$.

A transdermal drug delivery device in accordance with this invention containing diclofenac or its pharmaceutically acceptable salt can be used to treat any condition capable of treatment with this drug and in particular the treatment of inflammation and the relief of pain. The device can be placed on the skin and allowed to remain for a time sufficient to achieve or maintain the intended therapeutic effect. The time that constitutes a sufficient time can be selected by those skilled in the art with consideration of the flux rate of the device of the invention and upon the condition being treated.

The examples set forth below are intended to illustrate the invention, and not to limit it in any way.

In Vitro Skin Penetration Test Method

The skin penetration data given in the examples below was obtained using the following test method. A static diffusion cell (Franz-cell type) is used. Hairless mouse skin (female hairless mice, 3–4 weeks old) or human skin (obtained from surgery) is used. The skin is mounted epidermal side up between the upper and the lower portion of the cell, which are held together by means of a ball joint clamp.

The portion of the cell below the mounted skin is completely filled with receptor fluid "HEPES" (N-[2-hydroxyethyl]piperazine-N'-[2-ethanesulfonic acid]) buffered Hanks balanced salt solution, pH 7.2, supplemented with 4 ml of anti-biotic (A 7292 obtained from Sigma) per liter such that the receptor fluid is in contact with the skin. The receptor fluid is stirred using a magnetic stir bar. The sampling port is covered except when in use.

When a transdermal delivery device is evaluated, the release liner is removed from a 1.55 cm$^2$ patch and the patch is applied to the skin and pressed to cause uniform contact with the skin and then the skin is placed across the orifice of the lower portion of the diffusion cell. The diffusion cell is assembled and the lower portion is filled with receptor fluid.

The cell is then placed in a constant temperature (32±1.5° C.) and humidity (45±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (3, 6, 12, 24, 36 and 48 hours) and immediately replaced with fresh receptor fluid. The withdrawn receptor fluid is analyzed for drug content using conventional high performance liquid chromatography. The cumulative amount of drug penetrating the skin is calculated. The following abbreviations are used in the examples:

IPM: isopropyl myristate
PG: Propylene glycol
OCP: N-octylpyrrolidone
Diclofenac-Na: sodium salt of Diclofenac
IOA/AA-1: a copolymer of isooctyl acrylate and acrylic acid containing 90% by weight of isooctyl acrylate and 10% by weight of acrylic acid
IOA/AA-2: similar as IOA/AA but containing 94% by weight of isooctyl acrylate and 6% by weight of acrylic acid

EXAMPLE 1(COMPARATIVE)

To 123.6 g of a solution containing 16% by weight of IOA/AA-1 in ethylacetate, 1.8 g diclofenac-Na, 9 g IPM, 16 g ethanol and 30 g n-hexane were added. Intimate mixing afforded a homogeneous coating solution.

The solution was coated onto a release liner (Scotchpak™ 1022) at a wet thickness of 900 µm and oven dried for 20 minutes at 60° C. The dried coatings were then laminated with Scotchpak™ 1109 backing. The resulting devices had a drug loading of 0.64 mg diclofenac-Na per 1 cm$^2$.

Samples of the device with a size of 1.55 cm² were tested with respect to the in-vitro penetration characteristics through human skin (obtained from surgery). The results are shown in Table 1 below where each drug penetration value is the average of four independent determinations.

EXAMPLE 2 (COMPARATIVE)

To 95.2 of a solution containing 20.8% by weight of IOA/AA-1 in ethylacetate, 1.8 g diclofenac-Na, 6.3 g IPM, 3.2 g PG and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Scotchpak™ 1109 backing. The resulting devices had a drug loading of 0.56 mg diclofenac-Na per 1 cm².

Samples of the device with a size of 1.55 cm² were tested with respect to the in-vitro penetration characteristics through human skin (obtained from surgery). The results are shown in Table 1 below where each drug penetration value is the average of four independent determinations.

EXAMPLE 3

To 90.2 g of a solution containing 22% by weight of IOA/AA-1 in ethylacetate, 1.8 g diclofenac-Na, 4.6 g IPM, 3.14 g PG, 1.55 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Scotchpak™ 1109 backing. The resulting devices had a drug loading of 0.58 mg diclofenac-Na per 1 cm².

Samples of the device with a size of 1.55 cm² were tested with respect to the in-vitro penetration characteristics through human skin (obtained from surgery). The results are shown in Table 1 below where each drug penetration value is the average of four independent determinations.

EXAMPLE 4

To 95.4 g of a solution containing 20.8% by weight of IOA/AA-1 in ethylacetate, 1.8 g diclofenac-Na, 5.72 g IPM, 3.1 g PG, 0.61 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Scotchpak™ 1109 backing. The resulting devices had a drug loading of 0.58 mg diclofenac-Na per 1 cm².

Samples of the device with a size of 1.55 cm² were tested with respect to the in-vitro penetration characteristics through human skin (obtained from surgery). The results are shown in Table 1 below where each drug penetration value is the average of four independent determinations.

EXAMPLE 5

To 58.3 g of a solution containing 34% by weight of IOA/AA-2 in ethylacetate, 1.8 g diclofenac-Na, 4.6 g IPM, 3.15 g PG, 1.6 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Scotchpak™ 1109 backing. The resulting devices had a drug loading of 0.58 mg diclofenac-Na per 1 cm².

Samples of the device with a size of 1.55 cm² were tested with respect to the in-vitro penetration characteristics through human skin (obtained from surgery). The results are shown in Table 1 below where each drug penetration value is the average of four independent determinations.

TABLE 1

| Example | Adhesive | Enhancers (wt. %) | Coating (mg/cm²) | Drug loading (mg/cm²) | Drug penetration (μg/cm²* 24 h) |
|---|---|---|---|---|---|
| 1 | IOA/AA-1 | 30% IPM | 11 | 0.64 | 63.5 |
| 2 | IOA/AA-1 | 20% IPM 10% PG | 9.6 | 0.56 | 39.4 |
| 3 | IOA/AA-1 | 15% IPM 10% PG 5% OCP | 10 | 0.58 | 83.7 |
| 4 | IOA/AA-1 | 18% IPM 10% PG 2% OCP | 10 | 0.58 | 79.4 |
| 5 | IOA/AA-2 | 15% IPM 10% PG 5% OCP | 10 | 0.58 | 175 |

EXAMPLE 6 (COMPARATIVE)

To 96.2 g of a solution containing 20.6% by weight of IOA/EA-1 in ethylacetate, 1.8 g diclofenac-Na, 9 g IPM and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Cotran™ 9725 backing. The resulting devices had a drug loading of 0.58 mg diclofenac-Na per 1 cm².

Samples of the device with a size of 1.55 cm² were tested with respect to the in-vitro penetration characteristics through human skin (obtained from surgery). The results are shown in Table 2 below where each drug penetration value is the average of four independent determinations.

EXAMPLE 7

To 123.3 g of a solution containing 16.3% by weight of IOA/EA-1 in ethylacetate, 1.8 g diclofenac-Na, 6 g IPM, 3 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Cotran™ 9725 backing. The resulting devices had a drug loading of 0.52 mg diclofenac-Na per 1 cm².

Samples of the device with a size of 1.55 cm² were tested with respect to the in-vitro penetration characteristics through human skin (obtained from surgery). The results are shown in Table 2 below where each drug penetration value is the average of four independent determinations.

EXAMPLE 8

To 122.7 g of a solution containing 16.3% by weight of IOA/EA-1 in ethylacetate, 1.8 g diclofenac-Na, 4.5 g IPM, 3.0 g PG, 1.5 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Cotran™ 9725 backing. The resulting devices had a drug loading of 0.57 mg diclofenac-Na per 1 cm².

Samples of the device with a size of 1.55 cm² were tested with respect to the in-vitro penetration characteristics through human skin (obtained from surgery). The results are shown in Table 2 below where each drug penetration value is the average of four independent determinations.

EXAMPLE 9

To 123 g of a solution containing 16.3% by weight of IOA/EA- 1 in ethylacetate, 1.8 g diclofenac-Na, 5.4 g IPM, 3.0 g PG, 0.62 g OCP and 16 g ethanol were added. Intimate mixing afforded a homogeneous coating solution.

The solution was coated onto a release liner (Scotchpak™ 1022) at a wet thickness of 900 μm and oven dried for 20 minutes at 60° C. The dried coatings were then laminated with Cotran™ 9725 backing. The resulting devices had a drug loading of 0.59 mg diclofenac-Na per 1 cm².

Samples of the device with a size of 1.55 cm² were tested with respect to the in-vitro penetration characteristics through human skin (obtained from surgery). The results are shown in Table 2 below where each drug penetration value is the average of four independent determinations.

TABLE 2

| Example | Adhesive | Enhancers (wt. %) | Coating (mg/cm²) | Drug loading (mg/cm²) | Drug release (μg/cm²* 24 h) |
|---|---|---|---|---|---|
| 6 | IOA/AA-1 | 30% IPM | 10 | 0.58 | 6.0 |
| 7 | IOA/AA-1 | 20% IPM 10% OCP | 8.9 | 0.52 | 11.2 |
| 8 | IOA/AA-1 | 15% IPM 10% PG 5% OCP | 9.8 | 0.57 | 34.7 |
| 9 | IOA/AA-1 | 18% IPM 10% PG 2% OCP | 10 | 0.59 | 14 |

The present invention has been described in the foregoing specification and examples, which are provided for purposes of illustration and clarity of understanding only. No necessary limitations are to be drawn therefrom. It will be apparent to those skilled in the art that many changes can be made in the described embodiments without departing from the scope of the invention. Thus, the scope of the invention should not be limited to the exact details of the compositions and structures described herein, but is defined solely by the claims that follow.

What is claimed is:

1. A pressure sensitive skin adhesive comprising:
   (a) a copolymer of one or more alkyl(meth)acrylates containing 4 to 12 carbon atoms in the alkyl group and one or more hydrophilic monomers;
   (b) a mixture of penetration enhancers comprising:
      (i) an alkyl ester of an aliphatic monocarboxylic acid containing 1 to 5 carbon atoms in the alkyl group;
      (ii) an N-alkyl-2-pyrrolidone or a compound of the formula (I)

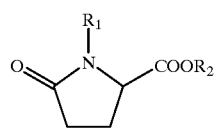

(I)

wherein $R_1$ is H or alkyl and $R_2$ is the residue of an aliphatic hydrocarbon and
      (iii) an alkane polyol; and
   (c) a therapeutically effective amount of diclofenac or a pharmaceutically acceptable salt thereof.

2. A pressure sensitive skin adhesive according to claim 1 wherein the weight ratio of monomer units derived from said alkyl(meth)acrylates to monomer units derived from said hydrophilic monomers in said copolymer is between 98:2 and 80:20.

3. A pressure sensitive skin adhesive according to claim 1 wherein said hydrophilic monomer is selected from the group consisting of carboxylic acid containing monomers, N-vinyl-2-pyrrolidone, vinylimidazoles, vinyl acetates, (meth)acrylamides, N-vinyl valerolactam, N-vinyl caprolactam, hydroxy containing monomers, mono-(meth) acrylates of poly(oxyalkylene), tetra-alkylammonium containing monomers and amino group containing monomers.

4. A pressure sensitive skin adhesive according to claim 1 wherein said hydrophilic monomer is selected from the group consisting of acrylic and methacrylic acid.

5. A pressure sensitive skin adhesive according to claim 1 wherein said alkane polyol is selected from the group consisting of propylene glycol and ethylene glycol.

6. A pressure sensitive skin adhesive according to claim 1 wherein said N-alkyl-2-pyrrolidone has 6 to 14 carbon atoms in the alkyl group.

7. A pressure sensitive skin adhesive according to claim 6 wherein said N-alkyl-2-pyrrolidone is N-octyl 2-pyrrolidone.

8. A pressure sensitive skin adhesive according to claim 1 wherein said alkyl ester of an aliphatic monocarboxylic acid is isopropyl myristate.

9. A pressure sensitive skin adhesive according to claim 1 wherein the total amount of said mixture of penetration enhancers is between 10 and 40% by weight of the total weight of said pressure sensitive skin adhesive.

10. A pressure sensitive skin adhesive according to claim 9 wherein said mixture of penetration enhancers comprises between 30 and 70% by weight of said alkyl ester of an aliphatic monocarboxylic acid; between 3 and 25% by weight of said N-alkyl-2-pyrrolidone or compound of the formula (I)

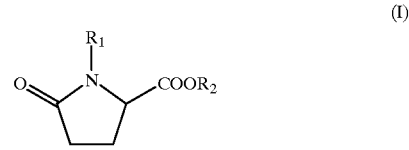

(I)

wherein $R_1$ is H or alkyl and $R_2$ is the residue of an aliphatic hydrocarbon; and between 20 and 45% by weight of said alkane polyol.

11. A pressure sensitive skin adhesive according to claim 1 wherein the diclofenac or pharmaceutically acceptable salt thereof is diclofenac sodium.

12. A pressure sensitive skin adhesive according to claim 1 wherein the diclofenac or pharmaceutically acceptable salt thereof is present in an amount of about 3 to 8 percent by weight based on the total weight of said pressure sensitive skin adhesive.

13. A transdermal drug delivery device comprising on a backing an adhesive layer comprising the pressure sensitive skin adhesive according to claim 1.

14. A method of treating inflammation or relieving pain in a subject comprising placing a pressure sensitive skin adhesive according to claim 1 in contact with the skin of the subject and allowing the pressure sensitive skin adhesive to remain in contact with the skin for a time effective to establish or maintain a therapeutically effective blood level of diclofenac or a pharmaceutically acceptable salt thereof in the subject.

* * * * *